(12) United States Patent
Wang et al.

(10) Patent No.: US 8,052,684 B2
(45) Date of Patent: Nov. 8, 2011

(54) IRRIGATED ABLATION CATHETER HAVING PARALLEL EXTERNAL FLOW AND PROXIMALLY TAPERED ELECTRODE

(75) Inventors: Huisun Wang, Maple Grove, MN (US); Christopher J. Geurkink, Minnetonka, MN (US); Harry Puryear, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 965 days.

(21) Appl. No.: 11/948,429

(22) Filed: Nov. 30, 2007

(65) Prior Publication Data
US 2009/0143779 A1    Jun. 4, 2009

(51) Int. Cl.
*A61B 18/18* (2006.01)
(52) U.S. Cl. ............................................. 606/49; 606/41
(58) Field of Classification Search .......... 600/372–381, 600/393; 604/528; 606/32, 34, 40–42, 49
See application file for complete search history.

(56) References Cited

U.S. PATENT DOCUMENTS

| | | | |
|---|---|---|---|
| 3,331,371 A | 7/1967 | Rocchi et al. |
| 3,671,979 A | 6/1972 | Moulopoulos |
| 4,026,298 A | 5/1977 | Grausz |
| 4,084,606 A | 4/1978 | Mittleman |
| 4,841,984 A | 6/1989 | Armeniades et al. |
| 4,857,054 A | 8/1989 | Helfer |
| 5,056,517 A | 10/1991 | Fenici |
| 5,061,823 A | 10/1991 | Carroll |
| 5,092,844 A | 3/1992 | Schwartz et al. |
| 5,230,349 A | 7/1993 | Langberg |
| 5,290,263 A | 3/1994 | Wigness et al. |
| 5,348,554 A | 9/1994 | Imran et al. |

(Continued)

FOREIGN PATENT DOCUMENTS
WO    96/36860 A2    11/1996
(Continued)

OTHER PUBLICATIONS

Wittkampf, et al., "Saline-Irrigated Radiofrequency Ablation Electrode with External Cooling," Journal of Cardiovascular Electrophysiology, vol. 16, No. 3, Mar. 2005.

(Continued)

*Primary Examiner* — Linda Dvorak
*Assistant Examiner* — Thomas Giuliani
(74) *Attorney, Agent, or Firm* — Armstrong Teasdale LLP

(57) ABSTRACT

Embodiments of the present invention provide an irrigated catheter having irrigation fluid directed at a taper angle generally in parallel with a proximally tapered portion of the tip electrode to provide improved electrode surface cooling. In one embodiment, an irrigated ablation electrode assembly for use with an irrigated catheter device comprises a proximal member having at least one passageway for a fluid with an outlet disposed at an external surface of the proximal member; and a distal member connected with the proximal member and having an external surface, the distal member including an electrode. The external surface of the distal member has a tapered proximal portion narrowing toward the proximal member at a taper angle with respect to a longitudinal axis of the distal member. The at least one passageway of the proximal member is configured to direct a fluid flow through the outlet in a distal direction at an angle substantially equal to the taper angle to produce an external flow that is generally parallel to the tapered proximal portion of the external surface of the distal member.

20 Claims, 5 Drawing Sheets

U.S. PATENT DOCUMENTS

| | | | |
|---|---|---|---|
| 5,403,276 A | 4/1995 | Schechter et al. | |
| 5,423,811 A | 6/1995 | Imran et al. | |
| 5,427,114 A | 6/1995 | Colliver et al. | |
| 5,456,682 A * | 10/1995 | Edwards et al. | 606/31 |
| 5,462,521 A | 10/1995 | Brucker et al. | |
| 5,545,161 A | 8/1996 | Imran | |
| 5,643,197 A | 7/1997 | Brucker et al. | |
| 5,660,205 A | 8/1997 | Epstein | |
| 5,688,267 A * | 11/1997 | Panescu et al. | 606/41 |
| 5,697,927 A | 12/1997 | Imran et al. | |
| 5,792,140 A | 8/1998 | Tu et al. | |
| 5,843,152 A | 12/1998 | Tu et al. | |
| 5,913,856 A | 6/1999 | Chia et al. | |
| 5,971,968 A | 10/1999 | Tu et al. | |
| 5,989,249 A | 11/1999 | Kirwan, Jr. | |
| 6,017,338 A | 1/2000 | Brucker et al. | |
| 6,044,845 A | 4/2000 | Lewis | |
| 6,050,986 A | 4/2000 | Hektner | |
| 6,080,151 A | 6/2000 | Swartz et al. | |
| 6,120,500 A | 9/2000 | Bednarek et al. | |
| 6,171,275 B1 | 1/2001 | Webster, Jr. | |
| 6,210,406 B1 | 4/2001 | Webster | |
| 6,217,573 B1 | 4/2001 | Webster | |
| 6,217,576 B1 | 4/2001 | Tu et al. | |
| 6,241,724 B1 | 6/2001 | Fleischman et al. | |
| 6,322,558 B1 | 11/2001 | Taylor et al. | |
| 6,425,894 B1 | 7/2002 | Brucker et al. | |
| 6,575,969 B1 | 6/2003 | Rittman, III et al. | |
| 6,602,242 B1 | 8/2003 | Fung et al. | |
| 6,611,699 B2 * | 8/2003 | Messing | 600/372 |
| 6,650,923 B1 | 11/2003 | Lesh et al. | |
| 6,659,959 B2 | 12/2003 | Brockway et al. | |
| 6,662,034 B2 | 12/2003 | Segner et al. | |
| 6,757,565 B2 | 6/2004 | Sharkey et al. | |
| 6,770,070 B1 | 8/2004 | Balbierz | |
| 6,852,120 B1 | 2/2005 | Fuimaono | |
| 6,855,143 B2 * | 2/2005 | Davison et al. | 606/41 |
| 6,955,675 B2 | 10/2005 | Jain | |
| 6,977,469 B2 | 12/2005 | Seinen et al. | |
| 6,984,232 B2 | 1/2006 | Vanney et al. | |
| 7,025,742 B2 | 4/2006 | Rubenstein et al. | |
| 7,166,105 B2 | 1/2007 | Mulier et al. | |
| 7,815,635 B2 * | 10/2010 | Wittkampf et al. | 606/41 |
| 2002/0177846 A1 | 11/2002 | Mulier et al. | |
| 2003/0014035 A1 | 1/2003 | Trombley, III et al. | |
| 2003/0069549 A1 | 4/2003 | MacMahon et al. | |
| 2003/0125726 A1 | 7/2003 | Maguire et al. | |
| 2003/0199867 A1 | 10/2003 | Wellman | |
| 2003/0225364 A1 | 12/2003 | Kraft et al. | |
| 2004/0030279 A1 | 2/2004 | Rubenstein et al. | |
| 2004/0054272 A1 | 3/2004 | Messing | |
| 2004/0098022 A1 | 5/2004 | Barone | |
| 2004/0102825 A1 | 5/2004 | Daoud | |
| 2004/0176801 A1 | 9/2004 | Edwards et al. | |
| 2004/0243121 A1 | 12/2004 | Lee et al. | |
| 2004/0267106 A1 | 12/2004 | Segner et al. | |
| 2005/0049453 A1 | 3/2005 | Faulkner | |
| 2005/0085769 A1 | 4/2005 | MacMahon et al. | |
| 2005/0137659 A1 | 6/2005 | Garabedian et al. | |
| 2005/0143798 A1 | 6/2005 | Bleam et al. | |
| 2005/0149116 A1 | 7/2005 | Edwards et al. | |
| 2005/0149166 A1 | 7/2005 | Schaeffer et al. | |
| 2005/0209580 A1 | 9/2005 | Freyman | |
| 2005/0256521 A1 | 11/2005 | Kozel | |
| 2005/0267467 A1 | 12/2005 | Paul et al. | |
| 2005/0273006 A1 | 12/2005 | Stewart et al. | |
| 2005/0288654 A1 | 12/2005 | Nieman et al. | |
| 2006/0036303 A1 | 2/2006 | Schwartz | |
| 2006/0058775 A1 | 3/2006 | Stevens et al. | |
| 2006/0058854 A1 | 3/2006 | Abrams et al. | |
| 2006/0089638 A1 | 4/2006 | Carmel et al. | |
| 2006/0229599 A1 | 10/2006 | Rashidi | |
| 2006/0278248 A1 | 12/2006 | Viswanathan | |
| 2006/0287650 A1 | 12/2006 | Cao et al. | |
| 2007/0270791 A1 * | 11/2007 | Wang et al. | 606/41 |
| 2008/0045943 A1 | 2/2008 | Wittkampf et al. | |
| 2008/0161794 A1 | 7/2008 | Wang et al. | |
| 2010/0152727 A1 * | 6/2010 | Gibson et al. | 606/41 |

FOREIGN PATENT DOCUMENTS

| | | |
|---|---|---|
| WO | 99/56812 A2 | 11/1999 |
| WO | 01/03589 A1 | 1/2001 |
| WO | 2005/048858 A1 | 6/2005 |
| WO | 2005/112814 A2 | 12/2005 |
| WO | 2009/023385 A1 | 2/2009 |
| WO | 2009/152151 A1 | 12/2009 |

OTHER PUBLICATIONS

Wittkampf, et. al., "Radiofrequency Ablation With a Cooled Porous Electrode Catheter," JACC, vol. 11, No. 2, Feb. 1988:17A Abstracts.

Soejima, et al., "Saline-cooled versus standard radiofrequency catheter ablation for infarct-related ventricular tachycardias"; Circulation, vol. 103, 2001, pp. 1858-1862.

Yokoyama, et al., Comparison of electrode cooling between internal and open irrigation in radiofrequency ablation lesion depth and incidence of thrombus and steam pop, Circulation, vol. 113, 2006, pp. 11-19.

Jais, et al., "Prospective Randomized Comparison of Irrigated-Tip Versus Conventional-Tip Cathethers for Ablation of Common Flutter"; Circulation, vol. 101, 2000, pp. 772-776.

Nakagawa, et al., "Inverse relationship between electrode size and lesion size during radiofrequency ablation with active electrode cooling"; Circulation, vol. 98, 1998, pp. 458-465.

Yamane, MD, et al., "Efficacy and safety of an irrigated-tip catheter for the ablation of accessory pathways resistant to conventional radiofrequency ablation"; Circulation, vol. 102, 2000, pp. 2565-2568.

Weiss, et al., "Radiofrequency catheter ablation using cooled electrodes: impact of irrigation flow rate and catheter contact pressure on lesion dimensions"; Pace, vol. 25, No. 4, Part 1, Apr. 2002, pp. 463-469.

International Searching Authority; PCT/US2007/088157; International Search Report dated May 13, 2008.

International Searching Authority; PCT/US2007/088157; Written Opinion dated May 13, 2008.

International Searching Authority; PCT/US2007/088136; International Search Report dated May 13, 2008.

International Searching Authority; PCT/US2007/088136; Written Opinion dated May 13, 2008.

International Searching Authority; PCT/US2007/088192; International Search Report dated Jun. 13, 2008.

International Searching Authority; PCT/US2007/088192; Written Opinion dated Jun. 13, 2008.

* cited by examiner

IRRIGATED ABLATION CATHETER HAVING PARALLEL EXTERNAL FLOW AND PROXIMALLY TAPERED ELECTRODE

CROSS-REFERENCE TO RELATED APPLICATIONS

This application is related to U.S. patent application Ser. No. 11/434,220, filed on 16 May 2006, to U.S. patent application Ser. Nos. 11/646,237, 11/646,255, 11/646,275, and 11/646,270, all filed on 28 Dec. 2006, and to concurrently filed, commonly assigned U.S. patent application Ser. No. 11/948,361, filed 30 Nov. 2007, entitled Irrigated Ablation Electrode Assembly and Method for Control of Temperature. The entire disclosures of the above applications are incorporated herein by reference.

BACKGROUND OF THE INVENTION a. Field of the Invention

The present invention pertains generally to ablation catheters and electrode assemblies. More particularly, the present invention is directed toward ablation electrode assemblies for use in the human body having a mechanism for irrigating targeted areas. The present invention also relates to methods for improved assembly and accurate measurement and control of the electrode temperatures while effectively irrigating the targeted areas.

b. Background Art

Electrophysiology catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart.

The catheter typically carries one or more electrodes, which may be used for ablation, diagnosis, or the like. There are a number of methods used for ablation of desired areas, including for example, radiofrequency (RF) ablation. RF ablation is accomplished by transmission of radiofrequency energy to a desired target area through an electrode assembly to ablate tissue at the target site.

Because RF ablation may generate significant heat, which if not carefully monitored and/or controlled can result in protein denaturation, blood coagulation, excess tissue damage, such as steam pop, tissue charring, and the like, it is desirable to monitor the temperature of the ablation assembly. It is further desirable to include a mechanism to irrigate certain target areas with biocompatible fluids, such as saline solution. This irrigation reduces or avoids excess, unwanted tissue damage, and blood coagulation and problems associated therewith. However, introduction of this irrigation solution may inhibit the ability to accurately monitor and/or control the temperature of the ablation assembly during use.

There are typically two classes of irrigated electrode catheters, open and closed irrigation catheters. Closed ablation catheters typically circulate a cooling fluid within the inner cavity of the electrode. Open ablation catheters, on the other hand, typically deliver the cooling fluid through open orifices on the electrode. Examples of these known catheters include the THERMOCOOL brand of catheters marketed and sold by Biosense-Webster. The current open irrigated ablation catheters use the inner cavity of the electrode, or distal member, as a manifold to distribute saline solution. The saline thus flows directly through the open orifices of the distal electrode member. This direct flow through the distal electrode tip lowers the temperature of the distal tip during operation, rendering accurate monitoring and control of the ablative process more difficult.

In these open electrode irrigated catheters, it has been determined that insulating the irrigation channels from the ablation electrode is beneficial. One such example was published on or around March 2005 in an article entitled "Saline-Irrigated Radiofrequency Ablation Electrode with Electrode Cooling," by Drs. Wittkampf and Nakagawa et al., the content of which is hereby incorporated by reference in its entirety. Similarly, the content of PCT International Publication No. WO 05/048858, published on Jun. 2, 2005, is hereby incorporated by reference in its entirety.

BRIEF SUMMARY OF THE INVENTION

Embodiments of the present invention provide an irrigated catheter configured to provide better electrode surface cooling and more accurate electrode tip temperature measurement. Moreover, the irrigation fluid is directed at target areas where coagulation is more likely to occur so as to minimize blood coagulation and the associated problems. In some embodiments, the invention further provides for significant improvements over known irrigation catheters, including those disclosed by Drs. Wittkampf and Nakagawa et al., by providing a multiple piece irrigated ablation electrode assembly that has the advantages of irrigating the target area while simultaneously improving the operation, temperature response, temperature monitoring and/or control mechanisms of the ablation assembly, so as to prevent unwanted, unnecessary tissue damage and blood coagulation. The present invention also provides for ablation electrode assemblies that are easier to manufacture and assemble than known irrigated ablation electrode assemblies.

The present invention is directed to improved irrigated ablation electrode assemblies and methods useful in conjunction with irrigated catheter and pump assemblies and RF generator assemblies designed to monitor and control the ablation process while minimizing blood coagulation and unnecessary tissue damage.

In accordance with an aspect of the present invention, an irrigated ablation electrode assembly for use with an irrigated catheter device comprises a proximal member having at least one passageway for a fluid with an outlet disposed at an external surface of the proximal member; and a distal member connected with the proximal member and having an external surface, the distal member including an electrode. The external surface of the distal member has a tapered proximal portion narrowing toward the proximal member at a taper angle with respect to a longitudinal axis of the distal member. The at least one passageway of the proximal member is configured to direct a fluid flow through the outlet in a distal direction at an angle substantially equal to the taper angle to produce an external flow that is generally parallel to the tapered proximal portion of the external surface of the distal member.

In some embodiments, the taper angle is about 5 degrees to about 25 degrees. The external surface of the distal member is electrically conductive, and has a longitudinal length of about 3 mm to about 6 mm. The at least one passageway of the proximal member is curved. The proximal member comprises a material having a thermal conductivity which is lower than a thermal conductivity of a material of the distal member. The distal member comprises an electrically conductive material. The distal member may comprise a material selected from the group consisting of platinum, gold, iridium, stainless steel, palladium and mixtures thereof.

In specific embodiments, the proximal member comprises an electrically nonconductive material. The proximal member may comprise a material selected from the group consisting of HDPE, polyimide, polyaryletherketones, polyetheretherketones, polyurethane, polypropylene, oriented polypropylene, polyethylene, crystallized polyethylene terephthalate, polyethylene terephthalate, polyester, ceramics, and plastics, and mixtures thereof.

In some embodiments, the external surface of the proximal member and the external surface of the distal member meet at an intersection, and wherein the outlet of the at least one passageway of the proximal member is disposed adjacent the intersection. A temperature sensor is disposed in the distal member along the longitudinal axis of the distal member. The distal member has an external surface that includes a rounded distal portion which is non-spherical. The proximal member includes a plurality of passageways distributed generally uniformly in a circumferential direction of the proximal member. The at least one passageway of the proximal member does not come into contact with any interior portion of the distal member.

In accordance with another aspect of the invention, an irrigated ablation electrode assembly for use with an irrigated catheter device comprises a distal portion including an electrode, and a proximal portion having at least one passageway for a fluid with an outlet disposed at an external surface of the irrigated ablation electrode assembly. The at least one passageway is configured to direct a fluid flow through the outlet in a distal direction at a taper angle with respect to a longitudinal axis of the irrigated ablation electrode assembly. The external surface adjacent and distal to the outlet is tapered to expand outwardly in the distal direction at an angle substantially equal to the taper angle to allow the at least one passageway to produce an external flow that is generally parallel to the tapered external surface adjacent and distal to the outlet.

In accordance with another aspect of the present invention, a catheter comprises a shaft; and an irrigated ablation electrode assembly coupled to a distal end of the shaft, the irrigated ablation electrode assembly having a distal portion which includes an electrode and a proximal portion which includes at least one passageway for a fluid with an outlet disposed at an external surface of the irrigated ablation electrode assembly. The at least one passageway is configured to direct a fluid flow through the outlet in a distal direction at a taper angle with respect to a longitudinal axis of the irrigated ablation electrode assembly. The external surface adjacent and distal to the outlet is tapered to expand outwardly in the distal direction at an angle substantially equal to the taper angle to allow the at least one passageway to produce an external flow that is generally parallel to the tapered external surface adjacent and distal to the outlet.

A technical advantage of the present invention is that the irrigated fluid is directed at a taper angle generally in parallel with a proximally tapered portion of the tip electrode to provide improved electrode surface cooling. In certain preferred embodiments, the electrode assembly thermally separates the cooling irrigation fluid from the distal electrode, as well as from the temperature sensing mechanism(s) within the distal member, thereby allowing for improved temperature control and/or monitoring while simultaneously allowing for irrigation of the target areas to minimize coagulation and unwanted tissue damage. The separation of the cooling fluid from the temperature sensing mechanisms further allows for better monitoring of rising temperature of the electrode assembly during operation, as well as other tell-tale factors of over-ablation of targeted tissue areas.

The foregoing and other aspects, features, details, utilities, and advantages of the present invention will be apparent from reading the following description and claims, and from reviewing the accompanying drawings.

DETAILED DESCRIPTION OF EXEMPLARY EMBODIMENTS

In general, the instant invention relates to irrigated ablation electrode assemblies, and to methods of manufacturing and using such irrigated ablation electrode assemblies. For purposes of this description, similar aspects among the various embodiments described herein will be referred to by the same reference number. As will be appreciated, however, the structure of the various aspects may be different among the various embodiments.

Figure 1:
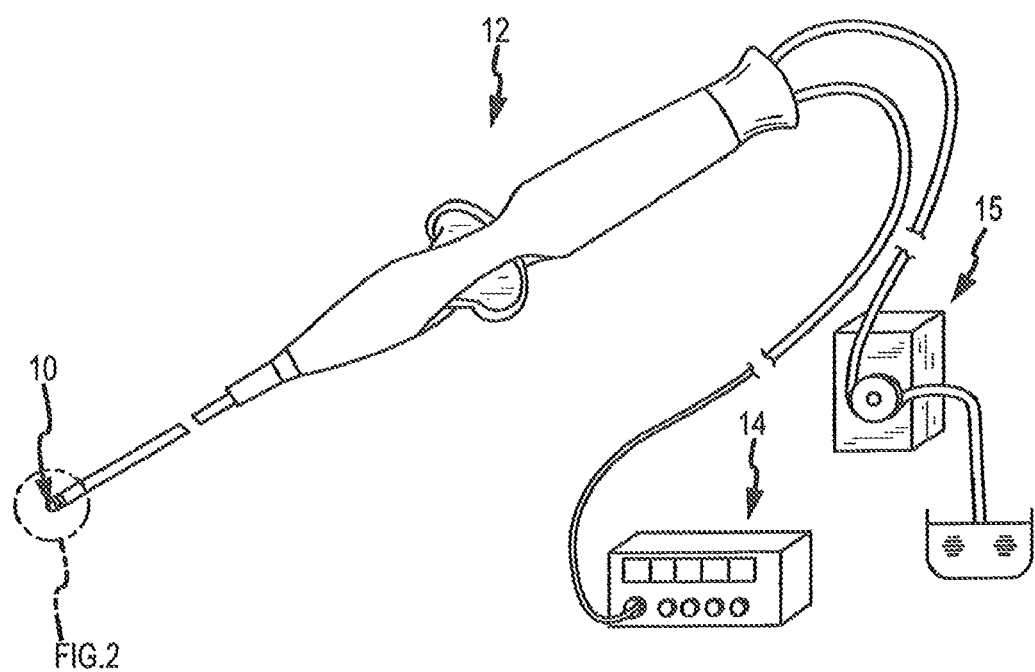
FIG. 1 is an isometric view of an ablation electrode assembly according to an embodiment of the present invention in conjunction with an irrigated catheter assembly operably connected to an RF generator assembly and a pump assembly.

As seen in FIG. 1, the ablation electrode assembly may comprise part of an irrigated ablation catheter assembly 12, operably connected to a pump assembly 15 and an RF generator assembly 14 which serves to facilitate the operation of ablation procedures through monitoring any number of chosen variables (e.g., temperature of the ablation electrode, ablation energy, and position of the assembly), assist in manipulation of the assembly during use, and provide the requisite energy source delivered to the electrode assembly 10. The present embodiments describe RF ablation electrode assemblies and methods, but it is contemplated that the present invention is equally applicable to any number of other ablation electrode assemblies where the temperature of the device and the targeted tissue areas is a factor during the procedure.

FIG. 1 is a general perspective view of an irrigated ablation catheter assembly having an RF generator assembly 14 and a fluid pump assembly 15 operably connected to an irrigation catheter assembly 12 having an irrigated electrode assembly 10 according to the present invention operably attached thereto. The structural and functional features of the catheter assembly 12 and the RF generator assembly 14 and pump assembly 15 are well-known to those of skill in the art. For example, the RF generator assembly could be an IBI-1500T RF Cardiac Ablation Generator available from Irvine Biomedical, Inc. in Irvine, Calif. 92614. The RF generator assembly could also be any other known assembly, including, for example, a Stockert RF generator available from Biosense, or one of the Atakr® series of RF generators available from Medtronic. The pump assembly can be any known assembly, including fixed volume rolling pumps, variable volume syringe pumps, and any other pump assembly known to those of skill in the art. FIGS. 2-7, discussed in more detail below, exemplify various embodiments of the irrigated ablation electrode assembly 10 according to the present invention.

Figure 2:
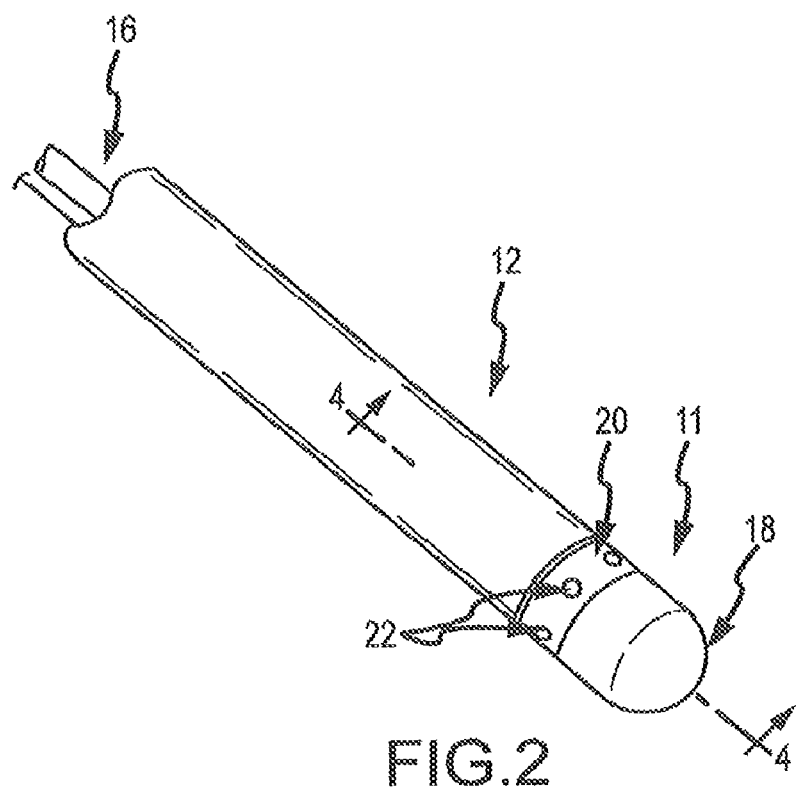
FIG. 2 is an enlarged, isometric view of the ablation electrode assembly according to an embodiment of the present invention operably connected to an irrigated catheter assembly.

FIG. 2 is an isometric view of an ablation electrode assembly 11 connected to an irrigated ablation catheter assembly 12 having a fluid delivery tube 16 therein. The ablation electrode assembly 11 generally comprises an irrigation member 20 and an ablation electrode member 18. The orientation of the members 18, 20 are generally such that the ablation electrode assembly 18 is situated at the distal end of the assembly with the irrigation member 20 located at the proximal end of the assembly, although it is conceivable the orientation could be reversed. The proximal member 20 has at least one passageway 24 (see FIG. 3) and at least one outlet 22 for delivery of a fluid to targeted tissue areas and the outside of the electrode assembly 11. The distal member 18 further comprises at least one temperature sensing mechanism 26 (see FIG. 3) disposed therein and operably connected to the RF generator assembly 14. The distal member 18 is comprised of any electrically, and potentially thermally, conductive material known to those of ordinary skill in the art for delivery of ablative energy to target tissue areas. Examples of the electrically conductive material include gold, platinum, iridium, palladium, stainless steel, and any mixtures thereof. Moreover, there are a number of electrode designs contemplated within the scope of the present invention including tip electrodes, ring electrodes, and any combination thereof.

In general accordance with the embodiments described herein, the fluid passageway(s) 24 and outlet(s) 22 are separated from the distal member 18, and accordingly the temperature sensing mechanism 26, by at least one poor thermally conductive material. A poor thermally conductive material is one with physical attributes that decrease heat transfer from the passageway(s) 24 to the distal member 18 by about 10% or more, and more preferably by about 25% or more measured by known methods to one of ordinary skill in the art. In particular embodiments, materials that decreased heat transfer by more than approximately 75% performed favorably. It is further contemplated that a poor thermally conductive material could have physical attributes that decrease heat transfer less than about 10%, provided that the remaining structural components are selected with the appropriate characteristics and sensitivities to maintain adequate monitoring and control of the process. Thus, while these properties are preferred, the poor thermally conductive material may be any material known to one of skill in the art consistent with the spirit of the invention. Examples of poor thermally conductive materials useful in conjunction with the present invention include, but are not limited to, HDPE, polyimides, polyaryletherketones, polyetheretherketones, polyurethane, polypropylene, oriented polypropylene, polyethylene, crystallized polyethylene terephthalate, polyethylene terephthalate, polyester, ceramics, and plastics such as Delrin®, and mixtures thereof.

As shown in more detail with respect to specific embodiments below, the poor thermally conductive material may be the material comprising the proximal member 20, or the distal member 18, a separate material from the proximal member 20 and the distal member 18, or any combination thereof. Additionally, the passageway(s) 24 and outlet(s) 22 defined by the proximal member 18 may also be separated longitudinally from the end 46 (see FIG. 3) of the distal member 18 thereby providing the benefit of insulating the passageway(s) 24 from the temperature sensor(s) 26 for improved temperature monitoring of the ablated target area during operation. The poor thermally conductive material, and the separation from the end 46 of the distal member 18, serve individually, and cooperatively, to minimize the effect of the lower temperature of the fluid delivered through the passageway(s) 24 and outlet(s) 22 from the temperature sensing mechanism(s) 26 within the distal member 18. The separation of the passageway(s) 24 and outlet(s) 22 from the distal member 18, and more particularly the temperature sensing mechanism 26, facilitate the dual purposes of (1) effectively irrigating the electrode assembly 10 and the targeted tissue area to minimize coagulation and unwanted tissue damage and (2) effectively controlling the operation of the ablation electrode assembly 10 in accordance with objects of the present invention.

Figure 3:
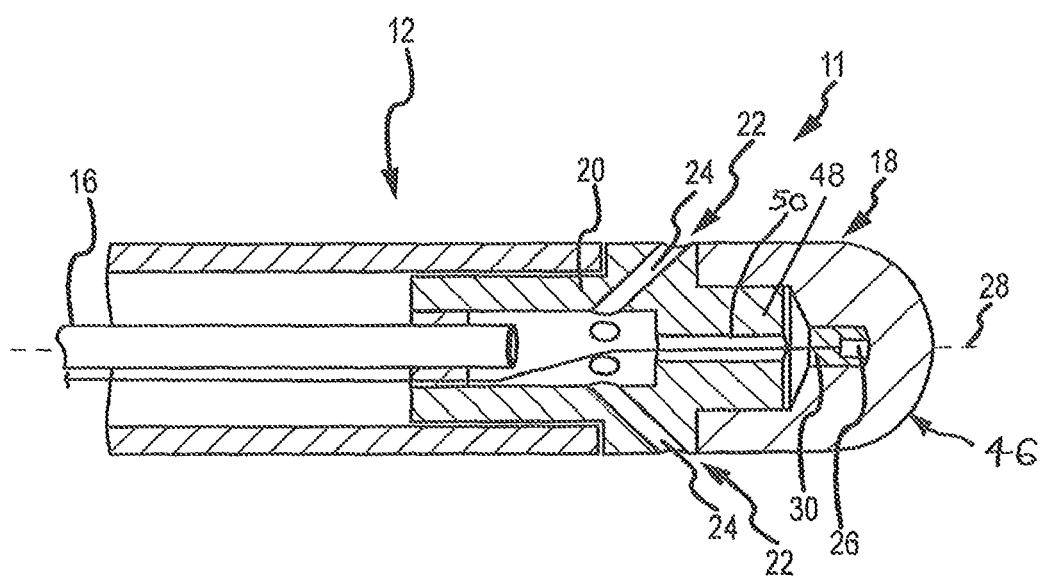
FIG. 3 is a cross-sectional view of the ablation electrode assembly of FIG. 2 taken along line 4-4 of FIG. 2.

FIG. 3 is a cross-sectional view of an embodiment of the ablation electrode assembly 11. FIG. 3 describes what is known to those in the art as a 2½ mm (length) ablation electrode assembly 10. A 2½ mm ablation electrode assembly 10 is often beneficial because it requires less power (around 10-20 W, as compared to around 20-40 W for a 4 mm assembly). However, it is contemplated that any size ablation electrode assembly 11, including a 4 mm assembly, is equally technically acceptable. In instances where a larger ablation area is desired to provide for different spatial orientation of the electrode assembly 11, a larger electrode surface area can be accommodated, while still yielding the desirable separation between the cooling passageways 24 and the temperature sensing mechanism 26.

As shown in FIG. 3, an ablation electrode assembly 11 is connected to an irrigation catheter assembly 12 having a fluid delivery tube 16. The ablation electrode assembly 11 comprises a proximal member 20, or manifold, a distal member 18, and a temperature sensing mechanism 26 operably connected to the RF generator assembly 14 (see FIG. 1). In this embodiment, the proximal member 20 itself is comprised of a poor thermally conducting material that serves to insulate the fluid from the remaining portions of the assembly 11. Preferably the proximal member 20 is made from a poor thermally conductive polymer, more preferably from a polyether ether ketone ("PEEK") because of this material's combination of thermal and physical properties. The proximal member 20 is configured to receive the fluid tube 16 of the catheter assembly 12 and comprises a plurality of passageways 24 extending from a central axis 28 of the assembly 11 axially toward the outer portion of the proximal member 20 terminating in corresponding outlets 22. Preferably, the plurality of passageways 24 are equally distributed around the proximal member 20 so as to provide equal distribution of fluid to the targeted tissue area and the outside of the assembly 11. The passageway 24 may be a single, annular passageway, or a number of individual passageways equally distributed around the proximal member 20. In this embodiment, the passageways 24 are at an acute angle with respect to the longitudinal axis 28 of the assembly 11. In operation, fluid is pumped through the delivery tube 16 and passes through the passageways 24 and through the outlets 22 where it contacts with targeted tissue areas and the outside portion of the ablation electrode assembly 11.

In this embodiment, the fluid delivery conduits 24, or passageways, extend at an angle substantially less than perpendicular to the longitudinal axis 28. Angling of the passageways 24 away from perpendicular, but less than parallel, further assists in the delivery of the fluid to the targeted tissue areas, further decreases the risk of coagulation of the bodily fluids during ablation procedures, and allows for improved measurement and control of the ablation assembly 11 during operation. More specifically, the passageways 24 are oriented to direct irrigation fluid flow at the target area adjacent, preferably immediately adjacent, the intersection between the proximal member 20 and the distal member 18. Blood coagulation is more likely to occur in the target area due to a sharp rise in RF intensity, material discontinuity, and potentially geometric discontinuity caused by manufacturing imperfection in joining the proximal member 20 and the distal member 18. In specific embodiments, the passageways 24 extend at an angle between approximately 20 and 70 degrees, preferably at an angle between approximately 30 and 60 degrees, and more preferably at an angle of approximately 30 degrees. It is also contemplated that the passageways may be further angled in a second dimension, such that the passageways and orifices are configured to provide fluid to the external portion of the assembly in a swirling, or helical fashion. This configuration also serves to keep the fluid in closer proximity to the electrode assembly, thereby further preventing against coagulation during operation.

The proximal member 20 is further configured to extend a portion 48 into the distal member 18 and has a pathway 50 for passage of the operable connection of the temperature sensing mechanism 26 within the distal tip 18. In this embodiment, this path 50 is shown extending substantially through the middle of the proximal member 20, but this path 50 can be located anywhere within or outside the proximal member 20. The resulting cross-sectional shape is substantially cross-shaped, in which the fluid passageways 24 and outlets 22 are isolated from other portions of the assembly 11 by the proximal member 20.

The distal member 18 of the ablation electrode assembly 11 has a generally cylindrical shape terminating in a hemispherical end. The distal member 18 is configured to accept a portion 48 of the proximal member 20 for attachment thereto. The distal member 18 may be connected to the proximal member 20 by any known mechanism including adhesives, press-fit configurations, snap-fit configurations, or the like.

The distal member 18 further contains at least one temperature sensing mechanism 26 disposed therein for measurement and control of the assembly 11 and targeted tissue areas during operation. FIG. 3 shows one temperature sensing mechanism 26 disposed along a longitudinal axis of the distal member 18. It is further contemplated that additional temperature sensing mechanisms can be utilized for further control and monitoring of the temperature of the assembly 11 at various additional locations. For purposes of the present invention, the temperature sensing mechanism(s) 26 can be any mechanism known to one of skill in the art, including for example, thermocouples or thermistors. In a further embodiment, the temperature sensing mechanism 26 is surrounded, or encapsulated, by a second thermally conductive and electrically non-conductive material 30. This thermally conductive and electrically non-conductive material 30 serves to hold the temperature sensing mechanism 26 in place within the distal tip 18 and provides excellent heat exchange between the temperature sensing mechanism 26 and the distal member. This material 30 may be comprised of a number of materials known to one of skill in the art, including for example, thermally conductive resins, epoxies, or potting compounds, such as the material sold under the trademark STYCAST 2651 MM.

Figure 4A:
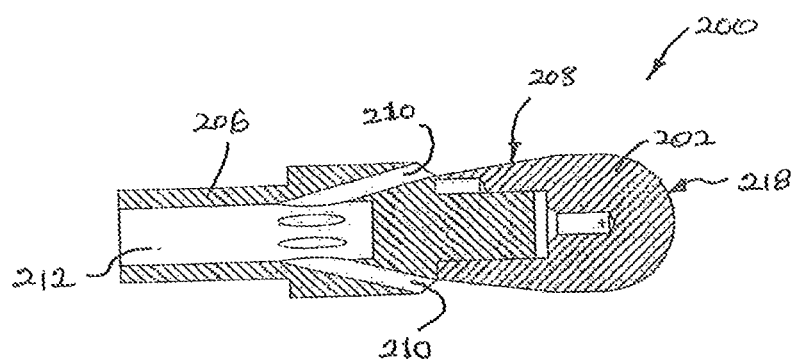
FIG. 4A is a cross-sectional view of an ablation electrode assembly according to another embodiment of the present invention.

FIG. 4A shows an ablation electrode assembly 200 having a distal member 202 and a proximal member 206. The embodiment of FIG. 4A differs from the one in FIG. 3 in that the distal member 202 has a different shape to provide an external surface having a tapered proximal portion 208 narrowing toward the proximal member 206 at a taper angle. The proximal member 206 is modified so that the irrigation fluid passageways 210 extending from the lumen 212 to the external surface are angled to direct irrigation fluid flow generally in parallel with the tapered proximal portion 208 of the distal member 202. In FIG. 4A, the inclined angle of the fluid passageways 210 and the taper angel of the tapered proximal portion 208 are substantially the same (e.g., within about 20% deviation, more preferably within about 10%). In specific embodiments, the taper angle is about 5 to about 25 degrees. The proximal passageways 210 preferably are angled toward the area of intersection between the proximal member 206 and the distal member 202. The external surface of the proximal member 206 and the external surface of the distal member 202 meet at an intersection, and the outlets of the proximal passageways 210 are disposed adjacent the intersection. The catheter shaft (not shown) is connected to the proximal member 206. The proximal member 206 is connected to the distal electrode 202. A power wire (not shown) supplies power to the distal electrode 202. A temperature sensing mechanism (not shown) is disposed along a longitudinal axis of the distal member 202. See FIG. 3.

The distal member 202 has a rounded distal portion 218 that may be spherical or non-spherical. The distal member 202 has an electrically conductive external surface, and may be made of an electrically conductive material such as platinum, gold, iridium, stainless, palladium, or the like. The longitudinal length of the distal member 202 along its longitudinal axis between the proximal end and the distal end is typically about 3 mm to about 6 mm, but may be shorter or longer. The proximal member 206, in contrast, is made of an electrically nonconductive material.

Figure 4B:
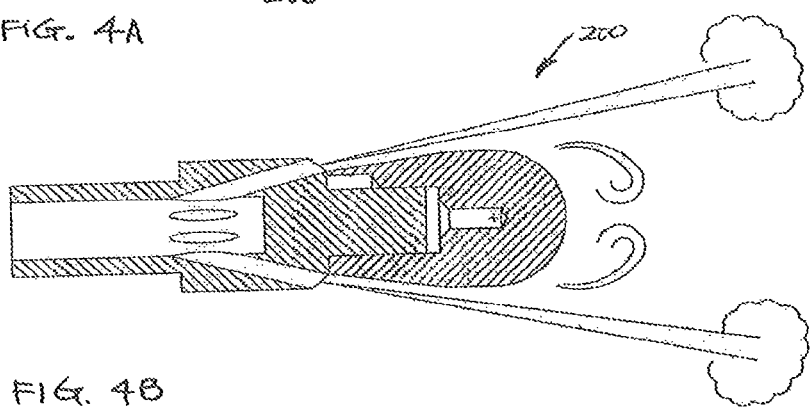
FIG. 4B illustrates schematically the irrigated fluid flow.

One benefit of the generally parallel flow design is that it provides adequate surface cooling and washing of the distal electrode 202 having a greater longitudinal length than previously possible without the use of parallel irrigation flow. As illustrated in FIG. 4B, the irrigation fluid flow remains in substantial contact with the proximal portion 208 of the external surface of the distal member 202 due to the generally parallel flow to the tapered proximal portion 208. During flow visualization tests, it was observed that the relatively shallow taper angle also generated fluid flow partially converging toward the distal portion 218 of the distal member 202. In the tests, the longitudinal length of the distal member 202 is about 3-8 mm, the taper angle of the tapered proximal portion 208 is about 5-20 degrees, and the irrigation fluid flow rate is about 10-20 ml/min. As a result, the irrigation fluid provides surface cooling of the distal member 202 and surface washing that lowers the concentration of blood flow in contact with or in close proximity to the surface of the distal member 202. This washing effect or diluting effect lowers the risk of coagulation at or near the surface of the distal member 202. In one preferred embodiment, the longitudinal length of the distal member 202 is about 4 mm, the taper angle is about 15 degrees, and the irrigation fluid flow rate is about 17 ml/min.

Figure 5A:
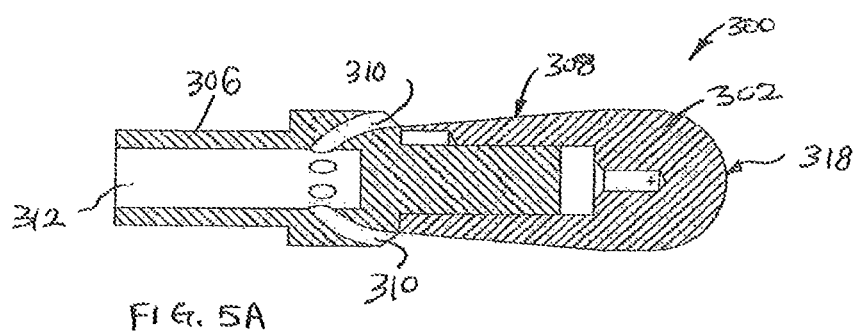
FIG. 5A is a cross-sectional view of an ablation electrode assembly according to another embodiment of the present invention.
Figure 5B:
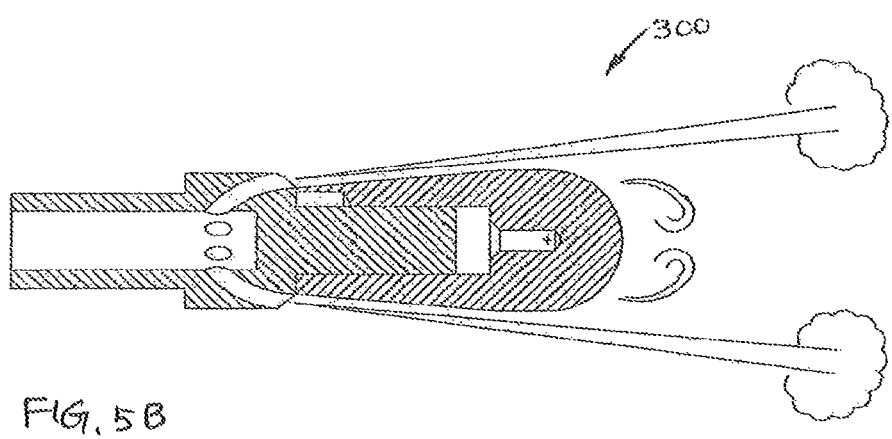
FIG. 5B illustrates schematically the irrigated fluid flow.

FIG. 5A shows an ablation electrode assembly 300 having a distal member 302 and a proximal member 306. The distal member 302 has a greater longitudinal length than the one in FIG. 4A. To keep the transverse dimension at about the same size, the tapered proximal portion 308 of the distal member 302 has a smaller taper angle than the one in FIG. 4A. The proximal passageways 310 in the proximal member 306 are curved to achieve the desired inclined angle of the fluid flow without significantly lengthening the proximal member 306. Irrigation fluid flows from the lumen 312 through the proximal passageways 310 to cool and wash the tapered proximal portion 308 of the distal member 302 in a substantially parallel flow pattern, as seen in FIG. 5B. A portion of the flow converges at a distal portion 318 of the distal member 302 to cool and wash the distal tip.

Figure 6A:
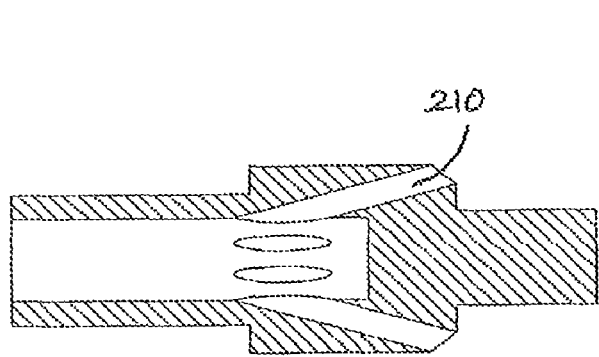
FIG. 6A is a cross-sectional view of a proximal member of the ablation electrode assembly of FIG. 4A.
Figure 6B:
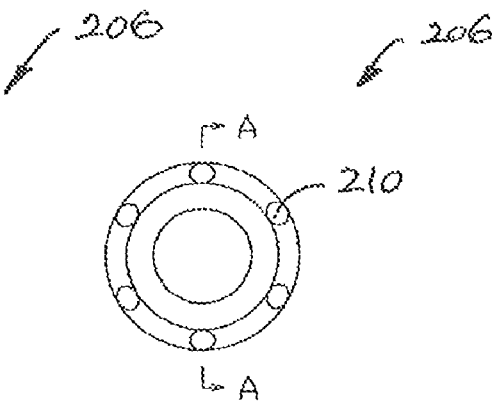
FIG. 6B is an end view of the proximal member.

FIGS. 6A and 6B show the proximal member 206 of FIG. 4A in greater detail. In this embodiment, there are six proximal passageways 210 distributed uniformly around the circumference of the proximal member 206. There can be fewer or more passageways 210 in other embodiments. The passageways 210 may be circular or noncircular in cross section (e.g., oval). The size of the passageways 210 should be large enough to avoid clogging and small enough to produce the desired flow rate for electrode surface cooling and washing without introducing an excessively large amount of irrigation fluid into the patient's body. For the embodiment shown, the desired flow rate is typically about 13-17 ml/min, and the passageways 210 are typically about 0.01-0.016 inches in diameter.

Figure 7A:
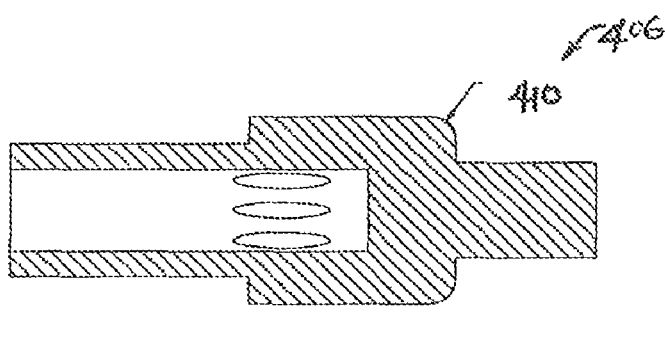
FIG. 7A is a cross-sectional view of a proximal member of an ablation electrode assembly according to another embodiment of the present invention.
Figure 7B:
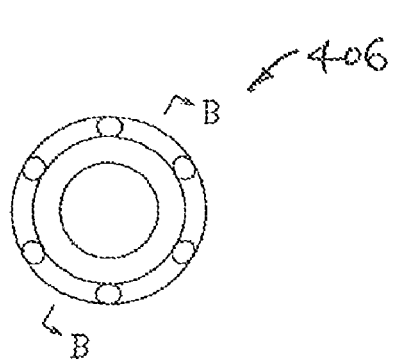
FIG. 7B is an end view of the proximal member.

FIGS. 7A and 7B show a proximal member 406 having a rounded corner 410 instead of the chamfered corner of the proximal member 206 in FIG. 6A. The rounded corner 410 may be considered more atraumatic than the chamfered corner.

Each of the proximal members (206, 306, 406) as described above preferably is made of a material having a thermal conductivity that is lower, more preferably substantially lower, than the thermal conductivity of the material of the corresponding distal member (202, 302). The proximal passageways (210, 310) do not come into contact with any exterior portion of the distal members. In this way, the irrigation fluid flowing through the proximal passageways is substantially insulated from the electrode and the temperature sensor of the distal member by distance and material of poor conductivity. The proximal members may be made of a variety of materials that have insulating properties such as, for example, DELRIN®, polyetheretherketone (PEEK), and high-density polyethylene (HDPE), as well as other materials of poor thermal conductivity mentioned above.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An irrigated ablation electrode assembly for use with an irrigated catheter device, the irrigated ablation electrode assembly comprising:

a proximal member having at least one passageway for a fluid with an outlet disposed at an external surface of the proximal member; and a distal member connected with the proximal member and having an external surface, the distal member including an electrode;

wherein the external surface of the distal member has a tapered proximal portion narrowing toward the proximal member at a taper angle with respect to a longitudinal axis of the distal member; and wherein the at least one passageway of the proximal member is configured to direct a fluid flow through the outlet in a distal direction at an angle substantially equal to the taper angle to produce an external flow that is generally parallel to the tapered proximal portion of the external surface of the distal member.

2. The irrigated ablation electrode assembly of claim 1 wherein the taper angle is about 5 degrees to about 25 degrees.

3. The irrigated ablation electrode assembly of claim 1 wherein the external surface of the distal member is electrically conductive, and has a longitudinal length of about 3 mm to about 6 mm.

4. The irrigated ablation electrode assembly of claim 1 wherein the at least one passageway of the proximal member is curved.

5. The irrigated ablation electrode assembly of claim 1 wherein the proximal member comprises a material having a thermal conductivity which is lower than a thermal conductivity of a material of the distal member.

6. The irrigated ablation electrode assembly of claim 1 wherein the distal member comprises an electrically conductive material.

7. The irrigated ablation electrode assembly of claim 1 wherein the distal member comprises a material selected from the group consisting of platinum, gold, iridium, stainless steel, palladium and mixtures thereof.

8. The irrigated ablation electrode assembly of claim 1 wherein the proximal member comprises an electrically nonconductive material.

9. The irrigated ablation electrode assembly of claim 1 wherein the proximal member comprises a material selected from the group consisting of HDPE, polyimide, polyaryletherketones, polyetheretherketones, polyurethane, polypropylene, oriented polypropylene, polyethylene, crystallized polyethylene terephthalate, polyethylene terephthalate, polyester, ceramics, and plastics, and mixtures thereof.

10. The irrigated ablation electrode assembly of claim 1 wherein the external surface of the proximal member and the external surface of the distal member meet at an intersection, and wherein the outlet of the at least one passageway of the proximal member is disposed adjacent the intersection.

11. The irrigated ablation electrode assembly of claim 1 further comprising a temperature sensor disposed in the distal member along the longitudinal axis of the distal member.

12. The irrigated ablation electrode assembly of claim 1 wherein the distal member has an external surface that includes a rounded distal portion which is non-spherical.

13. The irrigated ablation electrode assembly of claim 1 wherein the proximal member includes a plurality of passageways distributed generally uniformly in a circumferential direction of the proximal member.

14. The irrigated ablation electrode assembly of claim 1 wherein the at least one passageway of the proximal member does not come into contact with any interior portion of the distal member.

15. An irrigated ablation electrode assembly for use with an irrigated catheter device, the irrigated ablation electrode assembly comprising:

a distal portion including an electrode; and a proximal portion having at least one passageway for a fluid with an outlet disposed at an external surface of the irrigated ablation electrode assembly;

wherein the at least one passageway is configured to direct a fluid flow through the outlet in a distal direction at a taper angle with respect to a longitudinal axis of the irrigated ablation electrode assembly; and wherein the external surface adjacent and distal to the outlet is tapered to expand outwardly in the distal direction at an angle substantially equal to the taper angle to allow the at least one passageway to produce an external flow that is generally parallel to the tapered external surface adjacent and distal to the outlet.

16. The irrigated ablation electrode assembly of claim 15 wherein the taper angle is about 5 degrees to about 25 degrees.

17. The irrigated ablation electrode assembly of claim 15 further comprising a temperature sensor disposed in the distal member along the longitudinal axis of the irrigated ablation electrode assembly.

18. A catheter comprising:

a shaft; and an irrigated ablation electrode assembly coupled to a distal end of the shaft, the irrigated ablation electrode assembly having a distal portion which includes an electrode and a proximal portion which includes at least one passageway for a fluid with an outlet disposed at an external surface of the irrigated ablation electrode assembly;

wherein the at least one passageway is configured to direct a fluid flow through the outlet in a distal direction at a taper angle with respect to a longitudinal axis of the irrigated ablation electrode assembly; and wherein the external surface adjacent and distal to the outlet is tapered to expand outwardly in the distal direction at an angle substantially equal to the taper angle to allow the at least one passageway to produce an external flow that is generally parallel to the tapered external surface adjacent and distal to the outlet.

19. The catheter of claim 18 wherein the taper angle is about 5 degrees to about 25 degrees.

20. The catheter of claim 18 wherein the irrigated ablation electrode assembly further comprises a temperature sensor disposed in the distal member along the longitudinal axis of the irrigated ablation electrode assembly.

* * * * *